United States Patent [19]

Wierenga et al.

[11] Patent Number: 4,795,812

[45] Date of Patent: Jan. 3, 1989

[54] 4-SUBSTITUTED-6-ARYL-PYRIMIDINE COMPOUNDS

[75] Inventors: Wendell Wierenga; Harvey I. Skulnick, both of Oshtemo Township, Kalamazoo County, Mich.

[73] Assignee: The Upjohn Company, Kalamazoo, Mich.

[21] Appl. No.: 913,882

[22] Filed: Jan. 23, 1986

[86] PCT No.: US86/00074

§ 371 Date: Sep. 22, 1986

§ 102(e) Date: Sep. 22, 1986

[87] PCT Pub. No.: WO86/04583

PCT Pub. Date: Aug. 14, 1986

Related U.S. Application Data

[63] PCT US86/00074 is a continuation-in-part of Ser. No. 698,309, Feb. 5, 1985, abandoned.

[51] Int. Cl.[4] ................. C07D 239/42; C07D 239/48
[52] U.S. Cl. ..................................... 544/323; 514/908; 544/330
[58] Field of Search ............... 544/320, 324, 321, 323, 544/330; 514/275

[56] References Cited

U.S. PATENT DOCUMENTS

3,412,094  11/1968  Rorig et al. ......................... 544/324

FOREIGN PATENT DOCUMENTS

2048250  12/1980  United Kingdom ................ 544/324

OTHER PUBLICATIONS

Wierenga et al, *Chemical Abstracts*, vol. 95, No. 43025r (1981).

*Primary Examiner*—Robert W. Ramsuer
*Attorney, Agent, or Firm*—William G. Jameson

[57] ABSTRACT

This invention describes the synthesis and anti-neoplastic use of 4-aziridyl-5-substituted/unsubstituted 6-aryl-pyrimidine compounds of Formula IA

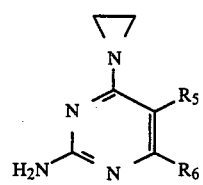

as well as N'-[2-(1-aziridyl)ethyl]-6-aryl-2,4-pyrimidinediamines of Formula IB

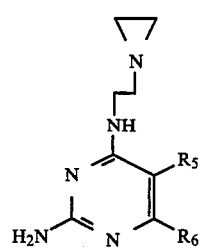

and 4-chloro or bromo-5-substituted/unstubstituted-6-aryl-pyrimidines.

9 Claims, No Drawings

4-SUBSTITUTED-6-ARYL-PYRIMIDINE COMPOUNDS

PCT US86/00074 is a continuation-in-part of Ser. No. 698,309 filed Feb. 5, 1985, now abandoned.

BACKGROUND OF THE INVENTION

Traditional treatments of cancer have utilized surgery, irradiation and chemotherapy. New classes of compounds are developed for use as chemotherapeutic agents. 5-Fluorouracil is a well known and widely used antineoplastic agent. Wierenga et al. disclose the use of 2-amino-6-aryl-5-substituted-4-pyrimidinols (pyrimidines) as interferon inducers, antiviral agents and for treatment of cancer in Belgium Pat. No. 882,315 and Great Britain Pat. No. 2,048,250.

The preparation of 4-chloro-6-phenyl-2-pyrimidinamine by the chlorination of 2-amino-6-phenyl-4(3H)-pyrimidinone with phosphorus oxychloride is described by Wierenga et al in Synthesis of 2-amino-6-phenyl-4(3H)-pyrimidinone-1-oxide, Heterocycles, 16(4), 563–71 (1981) and Chemical Abstracts 95 (5): 43025r.

4-Chloro-6-phenyl-2-pyrimidinamine is also disclosed in Heterocycles, 8, 229–305 (1977), Chemical Abstracts 88(15): 105255g and Izv. Akad. Nauk SSSR, Ser. Khim., 10, 2173–6 (1971), Chemical Abstracts 76(9): 45330t.

There are a number of examples of aziridine-containing anticancer agents, including triethylenemelamine, triethylenethiophosphoramide (thio-TEPA), aziridylbenzoquinone, mitomycins and 1-(2,3,5-tribenzoyl-$\beta$-1)-ribofuranosyl)-4-aziridil-2-pyrimidinone. See W. B. Pratt and R. W. Ruddon, *The Anti-Cancer Drugs*, Oxford Univ. Press, N.Y., 1979 and S. K. Carter, et al (ed.), *Recent Results in Cancer Research*, Springer-Verlag, Berlin, 1977 for a review.

BRIEF DESCRIPTION OF THE INVENTION

This application relates to 4-substituted-5-substituted-/unsubstituted-6-aryl-pyrimidine compounds represented by Formula I, wherein $R_4$ is chloro, bromo, aziridyl or 2-(1-aziridyl)ethylamino and $R_5$ and $R_6$ are as defined below, and the use thereof to treat an animal or human hosting a neoplastic disease.

DETAILED DESCRIPTION OF THE INVENTION

The 4-substituted-6-aryl-pyrimidine compounds represented by Formula I, including the 4-aziridyl-6-aryl-pyrimidine compounds represented by Formula IA and the N'-[2-(1-aziridyl)ethyl]-6-aryl-2,4-pyrimidinediamine compounds represented by Formula IB wherein $R_5$ is hydrogen, fluoro, chloro, bromo or iodo and $R_6$ is a member selected from the group consisting of (a) phenyl,
(b) a monosubstituted phenyl of Formula A wherein one of the Groups, X, $X_1$, $X_2$, $X_3$ or $X_4$ is not hydrogen and is fluoro, chloro, bromo, iodo, alkyl of from 1 to 5 carbon atoms, inclusive, including isomeric forms, alkoxy of from 1 to 5 carbon atoms, inclusive, including isomeric forms, nitro or dialkylamino of from 1 to 3 carbon atoms, inclusive, including isomeric forms, and
(c) a disubstituted phenyl of Formula A wherein any two of X, $X_1$, $X_2$, $X_3$ and $X_4$ are not hydrogen and are the same or different and are fluoro, chloro, bromo, iodo, alkyl of from 1 to 5 carbon atoms, inclusive, including isomeric forms, alkoxy of from 1 to 5 carbon atoms, inclusive, including isomeric forms, nitro or dialkylamino of from 1 to 3 carbon atoms, inclusive, including isomeric forms, and are prepared from 6-aryl-pyrimidinol compounds of Formula II by the procedures illustrated in Chart A.

The 6-aryl-pyrimidinol compounds are, however, tautomeric and can therefore also be drawn and/or named as isocytosines (Formula IIB), for example 2-amino-5-bromo-6-phenyl-4-pyrimidinol can also be named as 5-bromo-6-phenyl-isocytosine.

The 6-aryl-pyrimidinol compounds of Formula II can be obtained by the methods disclosed in Belgium Pat. No. 882,315 or Great Britain Pat. No. 2,048,250.

The starting 6-aryl-pyrimidinol (Formula II) is reacted with phosphorous oxychloride or phosphorous oxybromide, in the presence of heat to give the compound of Formula III where Z is chloro or bromo.

The compounds of Formula III, preferably where Z is chloro, is reacted with aziridine in the presence of an aprotic base, for example triethylamine, and carried out at 0° to 50°.

If the compounds of Formula III are unsubstituted at the 5-position, the compounds of Formula IA or IB can be halogenated, if desired, by well known art methods. See, Preparation III or IV and Chart B.

DEFINITIONS

The definitions and explanations below are for the terms as used throughout the entire patent application including both the specification and the claims.

All temperatures are in degree Centigrade.
TLC refers to thin-layer chromatography.
THF refers to tetrahydrofuran.
THP refers to tetrahydropyranyl.
DMSO refers to dimethylsulfoxide.
Skellysolve B refers to an isomeric mixture of hexanes.
DMA refers to dimethylacetamide.
NBS refers to N-bromosuccinimide.
NCS refers to N-chlorosuccinimide.
TEA refers to triethylamine.
Saline refers to an aqueous saturated sodium chloride solution.
IR refers to infrared spectroscopy.
CMR refers to $^{13}$C magnetic resonance spectroscopy, chemical shifts are reported in ppm ($\delta$) downfield from TMS.
NMR refers to nuclear (proton) magnetic resonance spectroscopy, chemical shifts are reported in ppm ($\delta$) downfield from tetramethylsilane.
TMS refers to trimethylsilyl.
MS refers to mass spectrometry expressed as m/e or mass/change unit.
Ether refers to diethyl ether.
Alcohol refers to ethyl alcohol.
Pharmaceutically acceptable refers to those properties and/or substances which are acceptable to the patient from a pharmacological-toxicological point of view and to the manufacturing pharmaceutical chemist from a physical-chemical point of view regarding composition, formulation, stability, patient acceptance and bioavailability.
When solvent pairs are used, the ratios of solvents used are volume/volume (v/v).
When the term "alkyl of 1 through 5 carbon atoms" is used, it means and includes isomers thereof where such exist.

The following Preparations and Examples are to be construed as merely illustrative of compounds of Formula I and means of preparing said compounds, and not limitative of the remainder of the disclosure.

Example 1

Synthesis of 4-chloro-6-phenyl-2-pyrimidinamine; 2-amino-4-chloro-6-phenylpyrimidine To 10.0 g (53 mM) of 6-phenylisocytosine is added 80 ml of phosphorus oxychloride. The mixture is heated to reflux, and refluxed until solution is complete (about 30 minutes). The solution is then cooled and evaporated to dryness under vacuum at 45° C. The resulting oil is poured into 300 ml of ice water, with vigorous stirring, and the remaining oil washed into the aqueous mixture with additional 100 ml of water. The entire aqueous mixture is neutralized to pH 8 with concentrated ammonium hydroxide, filtered, and solids washed well with water until water wash is neutral. Dry at 60° in a vacuum oven to yield 9.2 g of 4-chloro-6-phenyl-2-pyrimidinamine.

Example 2

4-(1-aziridyl)-6-phenyl-2-pyrimidinamine; 2-amino-4-(1-aziridyl)-6-phenylpyrimidine To 10.0 g (48.7 mM) of 4-chloro-6-phenyl-2-pyrimidinamine is added a solution of 10.25 ml of triethylamine (73 mM) in 50.0 ml of aziridine (965 mM). The mixture is stirred t 20° for 24 hours and evaporated, under vacuum to dryness (the distillate is collected in a trap that is cooled with a dry-ice/acetone bath, and then carefully discarded). The residue is dissolved in a minimum amount of methanol and poured into 1500 ml of ethyl acetate. The solids are filtered and the organic solution evaporated to dryness under vacuum. The residue is dissolved in 50.0 ml of ethyl acetate, placed on top of 500 g silica gel and eluted with ethyl acetate taking 50.0 ml fractions. The desired fractions are pooled (Rf 0.5 in ethyl acetate) and evaporated to dryness to yield 2.3 g of 4-(1-aziridyl)-6-phenyl-2-pyrimidinamine. m.p. 146°–147°.

Calculated for $C_{12}H_{12}N_4$: C, 67.90; H, 5.70; N, 26.40. Found: C, 67.72; H, 5.85; N, 26.29.

H" NMR ($d_6$ acetone): 8.16–7.96 7.63–7.36, 6.78, 2.26.

Example 3

4-(1-aziridyl)-5-bromo-6-phenyl-2-pyrimidinamine; 2-amino-4-(1-aziridyl)-5-bromo-6-phenylpyrimidine To 106 mg (0.5 mM) of 4-(1-aziridyl)-6-phenyl-2-pyrimidinamine is added 2 ml of dry N,N-dimethylformamide followed by 97 mg of N-bromosuccinimide. The reaction mixture is held at 20° for 96 hours. The mixture is evaporated to dryness under high vacuum and two ml's of 95% ethanol are added. The mixture is held at 20° for 1 hr, filtered, and the crystals washed with 95% ethanol to yield 30 mg of 4-(1-aziridyl)-5-bromo-6-phenyl-2-pyrimidinamine.

m.p. 160.5°–161°.

Calculated for $C_{12}H_{11}BrN_4$: C, 49.50; H, 3.81; N, 19.14; Br, 27.45. Found: C, 49.60; H, 4.08; N, 18.98; Br, 27.53.

H' NMR ($D_6$MSO): 7.65–7.3, 6.70, 2.35.

Example 4

Part I

Synthesis of 5-fluoro-6-phenylisocytosine

A. Preparation of ethyl-α-fluoro-benzoyl-acetate.

To 8.88 g NaH/oil is added 100 ml (diethyletherwashes) and decanted twice. An additional 100 ml of diethylether is added. With stirring, 20 g (188 mM) of ethylfluoroacetate is added dropwise, and when the addition is complete, the reaction is allowed to stir at ambient room temperature for 45 minutes.

Cooled to −50° and add 13.39 g (95 mm) benzoyl chloride, slowly, and with careful temperature control. When addition is complete the ice bath is removed and the reaction allowed to stir for an additional 45 minutes. The reaction mixture is poured into 400 ml of ice-cold ice/sulfuric acid, 100 ml diethylether added and the organic layer washed once with water, twice with saturated sodium bicarbonate, twice with water and dried over magnesium sulfate (anhydrous). Filtered, evaporated and distilled the residue at 3.5 mm gives 3.3 g (16%) of the fluoro β-keto ester, b.p. 94°–100° at 3.5 mm.

B. Synthesis of title compound.

To 575 mg (3.2 mM) of guanidine carbonate is added 40 ml of absolute ethanol+2 ml of toluene. Heated to reflux and azeotrop off 13 ml of solvent, cooled, and add 1.35 g (4 mM) of ethyl-α-fluoro-benzyl-acetate. Allow to heat at reflux, with continuous stirring, for 18 hours.

Add 25.0 ml of water, cooled, and neutralized by the addition of carbon dioxide chips. The solids are filtered and washed well with water followed by diethylether. The crude title compound is recrystallized from 95% ethanol to yield 260 mg mp 276°–8° of 2-amino-5-fluoro-6-phenyl-4(3H)-pyrimidinone; 5-ffluoro-6-phenylisocytosine.

Part II

Synthesis of 4-chloro-5-fluoro-6-phenyl-2-pyrimidinamine; 2-amino-4-chloro-5-fluoro-6-phenylpyrimidine To 200 mg of 5-fluoro-6-phenylisocytosine is added 12 ml of phosphorus oxychloride. The mixture is heated to reflux, and refluxed for ten minutes. The solution is then cooled and evaporated to dryness under vacuum, titrated with ice-water, neutralized with concentrated ammonium hydroxide added dropwise until the solution remains basic (pH~9) and stirred for a period of 30 minutes, the solids filtered, washed with water, and dried at 50° C. in a vacuum oven to yield 56 mg of 4-chloro-5-fluoro-6-phenyl-2-pyrimidinamine.

Calculated for $C_{10}H_7ClFN_3$: C, 53.70; H, 3.15; N, 18.79. Found: C, 50,77; H, 3.63; N, 18.68.

Example 5

Synthesis of N'-[2-(1-aziridyl)ethyl]-5-fluoro-6-phenyl-2,4-pyrimidinediamine.

To 50 mg (0.224 mM) of 4-chloro-5-fluoro-6-phenyl-2-pyrimidine is added 4.0 ml of aziridine and 1.01 ml of triethylamine. The reaction mixture is stirred at ambient temperature for 48 hrs. The solution is evaporated to dryness under high vacuum at 20°, and the residue is dissolved in minimal amount of ethyl acetate and chromatographed over 20 g of silica gel using 15% isopropanol/CHCl$_3$ as eluent. A fraction containing material with a TLC of 0.35 (15% MeOH/CHCl$_3$) is collected and evaporated to dryness to yield 18.0 mg of N'-[2-(1-aziridyl)ethyl]-5-fluoro-6-phenyl-2,4-pyrimidinediamine.

GC/MS (2'-1% Sf 30; 120°→250° @ 15°/minute).

m/e at 273; M-55.
High resolution mass spec MW calculated: 273.1389. Found: 273.1385.
H'-NMR (CDCl$_3$): δ 8.5–7.80 and 7.50–7.30; 5.70–5.50; 4.78; 3.65; 2.48; 1.90–1.7. 5 and 1.30–1.10.

Example 6

Synthesis of 5-bromo-4-chloro-6-phenyl-2-pyrimidinamine; 2-amino-5-bromo-4-chloro-6-phenylpyrimidine To 1.5 g (7.3 mM) of 4-chloro-6-phenyl-2-pyrimidinamine is added 75 ml of glacial acetic acid. This mixture is stirred to dissolve and 0.44 ml of bromine is added. The reaction is stirred at ambient temperature for 24 hours. The solution is evaporated to dryness under vacuum to yield 1.75 g of 5-bromo-4-chloro-6-phenyl-2-pyrimidinamine.
Calculated for $C_{10}H_7BrClN_3$: C, 42.20; H, 2.48; N, 14.77; Br, 28.10; Cl, 12.46. Found: C, 42.09; H, 2.59; N, 14.68; Br, 29.90; Cl, 11.05.
NMR H'-7.53.

Example 7

Synthesis of 4,5-dichloro-6-phenyl-2-pyrimidinamine

To 1.5 g (7.3 mM) of 4-chloro-6-phenyl-2-pyrimidinamine is added 40 ml of glacial acetic acid and 1.05 g of N-chlorosuccinimide. The reaction is stirred at ambient temperature ($-20°$ C.) for 18 hours. The reaction mixture is evaporated to dryness, dissolved in acetone and 10.0 g of silica gel added and the mixture evaporated to a powder under vacuum. The powder is chromatographed on 50 g silica gel and eluted with 35% ethyl acetate/hexane. A fraction containing material with a TLC r.f. of 0.7 35% ethylacetate/hexane is collected and evaporated to dryness, recrystallized from acetone/Skellysolve B (1:10), evaporated to dryness(?) to yield 0.90 g of 4,5-dichloro-6-phenyl-2-pyrimidinamine.
Calculated for $C_{10}H_7Cl_2N_3$: C, 50.03; H, 2.93; N, 17.50; Cl, 29.54. Found: C, 50.19; H, 2.98; N, 17.78; Cl, 29.50.
H'-NMR: 7.83–7.36; 5.8–5.55.

Example 8

Synthesis of 4-chloro-5-iodo-6-phenyl-2-pyrimidinamine; 2-amino-4-chloro-5-iodo-6-phenylpyrimidine To 3.12 g (10 mM) of 5-iodo-6-phenylisocytosine is added 30 ml of phosphorus oxychloride. The mixture is heated to dissolve, cooled to room temperature and evaporated to dryness under vacuum at 45° C. The resulting oil is added to 200 ml of water and the mixture neutralized by the addition of concentrated ammonium hydroxide. The solids are filtered, washed with water and dried at 50° C. in a vacuum oven for 18 hours, and then dissolved in acetone, filtered and 10.0 g of silica gel added and the mixture evaporated to a powder under a vacuum. The powder is chromatographed on 50 g silica gel and eluted with 35% ethyl acetate/hexane to yield, after crystallization from acetone/Skellysolve B (1:15), 0.6 g of 4-chloro-5-iodo-6-phenyl-2-pyrimidinamine.
Calculated for $C_{10}H_7ICIN_3$: C, 36.25; H, 2.12; N, 12.68; Cl, 10.70; I, 38.31. Found: C, 36.38; H, 2.17; N, 12.91; Cl, 10.91; I, 38.11.

ANTILEUKEMIA ACTIVITY 4-(1-aziridyl)-6-phenyl-2-pyrimidinamine, 4-(1-aziridyl)-5-bromo-6-phenyl-2-pyrimidinamine, N'-[2(1-aziridyl)ethyl]-5-fluoro-6-phenyl-2,4-pyrimidinediamine, 4-chloro-5-fluoro-6-phenyl-2-pyrimidinamine, 4,5-dichloro-6-phenyl-α-pyrimidinamine, 4-chloro-5-iodo-6-phenyl-2-pyrimidinamine, 5-bromo-4-chloro-6-phenyl-2-pyrimidinamine and 4-chloro-6-phenyl-2-pyrimidinamine, have been shown to inhibit the growth of L-1210 mouse leukemia cells in vitro as shown in Table I. The L-1210 tube dilution assay is described in detail in a publication by L. H. Li, et al, Cancer Research 39: 4816 (1979). ID$_{50}$ and ID$_{90}$ refer to the concentration of compound needed to inhibit cell growth by 50 and 90 percent, respectively.

4-(1-aziridyl)-6-phenyl-2-pyrimidinamine also demonstrated activity in vivo against P388 and L-1210 leukemias in mice but no in vivo activity in mice against B-16 melanoma. The P-388 mouse leukemia test is described in detail in a publication by G. L. Neil, et al, Cancer Treatment Reports 63, 1971–1978 (1979). The results of in vivo testing using different dosage schedules is shown in Table II.

The compounds of the subject invention (Formula I) or the pharmacologically acceptable acid addition salts thereof when R$_4$ is chloro or bromo, in association with a pharmaceutical carrier can be used to treat animals or humans hosting a neoplastic disease, for example, acute adenocarcinoma of lung, neuroblastoma, small cell carcinoma of lung, breast carcinoma, lymphomas, leukemias, colon carcinoma, ovarian carcinoma, bladder carcinoma, and the like. Suitable pharmacologically acceptable acid addition salts are, for example, the hydrochloride, sulfate, phosphate, nitrate, and the like. These salts can be used in the same manner as the base compounds.

The dosage administered will be dependent upon the identity of the neoplastic disease, the type of host involved, its age, health, weight, kind of concurrent treatment, if any, frequency of treatment and therapeutic ratio.

Illustratively, dosage levels of the administered active ingredients can be: intravenously or interaperitoneally at 10 to about 100 mg/kg/day intraperitoneally or orally at 10 to about 1000 mg/kg/day.

For humans, illustratively, dosage levels of the administered active ingredient can be: orally at 10 to about 1000 mg/kg/day, or preferably intravenously at 1 to about 100 mg/kg/day; the foregoing dose to be administered in one day. The dose can be readministered at daily intervals for 3–10 days for a course of therapy. Courses of therapy can be repeated at intervals, for example, every 4 weeks.

Expressed in terms of concentration, an active ingredient can be present in the compositions of the present invention in a concentration of from about 0.1 to about 90 percent w/w of the composition; preferably about 1 to about 20 percent w/w of the composition; and for parenteral use in a concentration of from about 0.5 to about 50 percent w/v of the composition and preferably from about 5 to about 20 percent w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted lactose or starch. Advantageously, a sweetening agent or sugar is present as well as a flavoring gel.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, coating of sugar and methylcellulose and a polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared by the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

The active ingredients can also be admixed in animal feed. The active ingredients can conveniently be prepared in the form of a food premix. The food premix can comprise an active ingredient in admixture with an edible pharmaceutical diluent such as starch, oatmeal, flour, calcium carbonate, talc, dried fish meal and the like nontoxic, orally acceptable pharmaceutical diluents. The prepared premix is then conveniently added to the regular feed.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, chachets, teaspoonfuls, tablespoonfuls, dropperfuls, ampules, vials, segregated multiples of any of the foregoing, and other forms as herein described.

The active ingredients to be employed can be easily prepared in unit dosage form with the employment of pharmaceutical materials which themselves are available in the art and can be prepared by established procedures. The following preparations are illustrative of the preparation of the unit dosage forms of the present invention, but are not intended to be limiting.

Example I

Hard-gelatin capsules

One thousand two-piece gelatin capsules for oral use, each capsule containing 100 mg of 4-(1-aziridyl)-6-phenyl-2-pyrimidinamine, are prepared from the following types and amounts of ingredients:

4-(1-aziridyl)-6-phenyl-2-pyrimidinamine, micronized: 100 gm
Lactose: 100 mg
Corn starch: 20 gm
Talc: 20 gm
Magnesium stearate: 2 gm The 4-(1-aziridyl)-6-phenyl-2-pyrimidinamine, finely divided by means of an air micronizer, is added to the other finely powdered ingredients, mixed thoroughly and then encapsulated in the usual manner.

The foregoing capsules are useful for treating lung cancer by the oral administration of one or two capsules one to four times a day.

Using the procedure above, capsules are similarly prepared containing 4-(1-aziridyl)-6-phenyl-2-pyrimidinamine in 50, 250 mg and 500 mg amounts by substituting 50 gm, 250 gm and 500 gm of 4-(1-aziridyl)-6-phenyl-2-pyrimidinamine for the 100 gm used above.

Example II

Soft gelatin capsules

One-piece soft gelatin capsules for oral use, each containing 250 mg of 4-(1-aziridyl)-6-phenyl-2-pyrimidinamine finely divided by means of an air micronizer, are prepared by first suspending the compound in 0.5 ml of corn oil to render the material capsulatable and then capsulating in the above manner.

The foregoing capsules are useful for treating lung cancer by the oral administration of one or two capsules one or four times a day.

Example III

Tablets

One thousand tablets, each containing 500 mg of 4-(1-aziridyl)-6-phenyl-2-pyrimidinamine, are prepared from the following types and amounts of ingredients:

4-(1-aziridyl)-6-phenyl-2-pyrimidinamine, micronized: 500 gm
Lactose: 75 gm
Corn Starch: 50 gm
Magnesium stearate: 4 gm
Light liquid petrolatum: 5 gm The 4-(1-aziridyl)-6-phenyl-2-pyrimidinamine, finely divided by means of an air micronizer, is added to the other ingredients and then thoroughly mixed and slugged. The slugs are broken down by forcing through a number sixteen screen. The resulting granules are then compressed into tablets, each tablet containing 500 mg of 4-(1-aziridyl)-6-phenyl-2-pyrimidinamine.

The foregoing tablets are useful for treating lung cancer by the oral administration by one or two tablets one to four times a day.

Using the procedure above, tablets are similarly prepared containing 4-(1-aziridyl)-6-phenyl-2-pyrimidinamine in 250 mg and 100 mg amounts by substituting 250 mg and 100 gm of 4-(1-aziridyl)-6-phenyl-2-pyrimidinamine for the 500 gm used above.

Example IV

Oral suspension

One thousand ml of an aqueous suspension for oral use, containing in each teaspoonful (5 ml) dose, 500 mg of 4-(1-aziridyl)-6-phenyl-2-pyrimidinamine, is prepared from the following types and amounts of ingredients:

4-(1-aziridyl)-6-phenyl-2-pyrimidinamine, micronized: 100 gm
Citric acid: 2 gm
Benzoic acid: 1 gm
Sucrose: 700 gm
Tragacanth: 5 gm
Lemon oil: 2 gm
Deionized water, q.s.: 1,000 ml The citric acid, benzoic acid, sucrose, tragacanth and lemon oil are dispersed in sufficient water to make 850 ml of suspension. The 4-(1-aziridyl)-6-phenyl-2-pyrimidinamine, finely divided by means of an air micronizer, is stirred into the syrup until uniformly distributed. Sufficient water is added to make 1,000 ml.

The composition so prepared is useful for treating leukemia at a dose of one tablespoonful (15 ml) three times a day.

Example V

A sterile aqueous suspension for parenteral injection, containing in one mg 300 mg of 4-(1-aziridyl)-6-phenyl-2-pyrimidinamine, is prepared from the following types and amounts of ingredients:

4-(1-aziridyl)-6-phenyl-2-pyrimidinamine, micronized: 300 gm
Polysorbate 80: 500 gm
Methylparaben: 2.5 gm
Propylparaben: 0.17 gm
Water for injection, q.s.: 1,000 gm All the ingredients except the 4-(1-aziridyl)-6-phenyl-2-pyrimidinamine are dissolved in the water and the solution sterilized by filtration. To the sterile solution is added the sterilized 4-(1-aziridyl)-6-phenyl-2-pyrimidinamine, finely divided by means of an air micronizer, and the final suspension is filled into sterile vials and the vials sealed.

The composition so prepared is useful for treating adenocarcinoma at a dose of one milliliter (1M) three times a day.

Example VI

Hard gelatin capsules

One thousand two-piece hard gelatin capsules for oral use, each capsule containing 100 mg of 4-(1-aziridyl)-6-phenyl-2-pyrimidinamine, are prepared from 100 gm of 4-(1-aziridyl)-6-phenyl-2-pyrimidinamine.

The 4-(1-aziridyl)-6-phenyl-2-pyrimidinamine is finely divided by means of an air micronizer and encapsulated in the usual manner.

The foregoing capsules are useful for preventing or treating metastasis following mastectomy by the oral administration of one or two capsules one to four times a day.

Using the procedure above, capsules are similarly prepared containing 4-(1-aziridyl)-6-phenyl-2-pyrimidinamine in 50 mg, 250 mg and 500 mg amounts by substituting 50 gm, 250 gm and 500 gm of 4-(1-aziridyl)-6-phenyl-2-pyrimidinamine for the 100 gm used above.

Example VII

Following the procedure of the preceding Examples 1 through 6, inclusive, compositions are prepared substituting equivalent amounts of the pharmaceutically acceptable acid addition salts of 4-(1-aziridyl)-6-phenyl-2-pyrimidinamine for the free base of the examples.

The antibacterial spectrum of 4-(1-azindinyl)-6-phenyl-2-pyrimidinamine was determined in an in vitro disk plate assay. The assay procedure is as follows:

A solution of 4-(1-aziridinyl)-6-phenyl-2-pyrimidinamine was prepared at 1 mg/ml in distilled water. Paper assay disks (½ inch) were dripped into the solution and spotted on seeded agar trays. The zones were read after 18 hours incubation and are reported in Table III.

In addition, the antibacterial spectrum of 4-chloro-6-phenyl-2-pyrimidinamine was determined in the above-identified in vitro disk plate assay and exhibited a zone of inhibition (20 mm) against *Proteus vulgaris*. No other antibacterial activity against the test organisms was observed.

Thus, these compounds are also useful to control the proliferation of susceptible microbes in various environments using standard microbiological techniques. Such environments include laboratory benches in a microbiological laboratory which can be cleansed with a formulation of these compounds.

A formulation of 4-(1-aziridinyl)-6-phenyl-2-pyrimidinamine can be used to cleanse food processing equipment and/or utensils contaminated by *Streptococcus pyogenes*. It is contemplated that formulations of other compounds of Formula IA can also be used in a like manner.

FORMULA
I
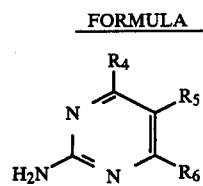
IA
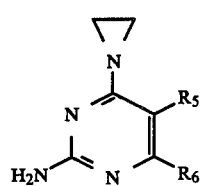
IB
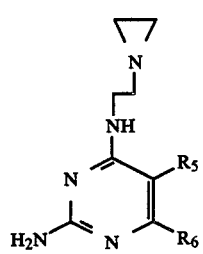
II
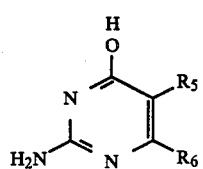
IIB
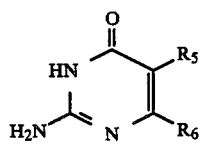
A
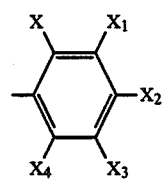
CHART A
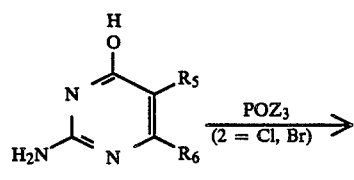
-continued
CHART A
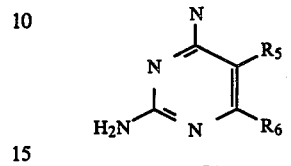
IA     IB
TABLE I
| Structure | L1210 ID$_{50}$ μg/ml | ID$_{90}$ μg/ml |
|---|---|---|
| 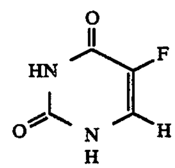 | 0.1 | 0.3 |
| 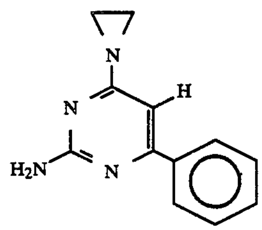 | 0.38 | 1.0 |
| 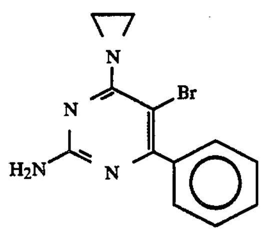 | 1.2 | 3.2 |
| 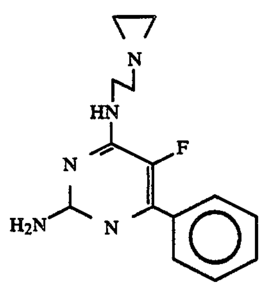 | 0.78 | 2.1 |
| 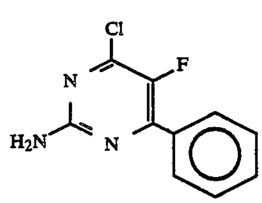 | 0.18 | 0.55 |

TABLE I-continued

| Structure | L1210 ID$_{50}$ μg/ml | ID$_{90}$ μg/ml |
|---|---|---|
| (2-amino-4-chloro-5-chloro-6-phenylpyrimidine) | 0.91 | 2.1 |
| (2-amino-4-chloro-5-iodo-6-phenylpyrimidine) | 1.8 | 3.9 |
| (2-amino-4-chloro-5-bromo-6-phenylpyrimidine) | 0.64 | 1.6 |
| (2-amino-4-chloro-6-phenylpyrimidine) | 8.2 | 19.0 |

TABLE II

| Tumor | Dose$^a$ | % ILS$^b$ | Weight Change$^c$ |
|---|---|---|---|
| i.p.-P388 | 40 | 47 | −3.8 |
| | 20 | 25 | −0.7 |
| | 10 | 11 | +2.1 |
| | 5 | 10 | +1.8 |
| i.p.-P388 | 40 | 26 | −2.0 |
| | 20 | 17 | +0.5 |
| | 10 | 11 | +2.1 |
| | 5 | 14 | +1.8 |
| i.p.-L1210 | 40 | 24 | −2.4 |
| | 20 | 9 | +0.6 |
| | 10 | 0 | +1.5 |
| | 5 | 0 | +1.2 |
| i.p.-B16 | 50 | 7 | −3.0 |
| | 25 | 11 | −0.5 |
| | 12.5 | 4 | +0.3 |
| | 6.3 | 2 | +1.2 |

$^a$mg/kg/day, daily × 9, i.p., administered as a Klucel Suspension.
$^b$% increase in life span of treated compared to control animals.
$^c$g/mouse between days 1 and 5 after tumor inoculation.

The NCI-designated criteria of significant activity for synthetic agents in these 3 systems are: for P388, 20% ILS; L1210 and B16, 25% ILS.

TABLE III

| Test Organism | Assay Medium | Zone of Inhibition (mm) |
|---|---|---|
| E. coli | B | 0 |
| S. schottmuelleri | B | 0 |
| B. fragilis | H | 23 |
| S. luteau | C | 0 |
| E. coli | E | 0 |
| S. pastorianus | G | 0 |
| P. vulgaris | B | 0 |

TABLE III-continued

| Test Organism | Assay Medium | Zone of Inhibition (mm) |
|---|---|---|
| S. lutea+ | C | 0 |
| Ps. aeruginosa | B | 0 |
| S. aureus | B | 0 |
| Rhodopseudomonas spheroides | F | 18 |
| K. pneumoniae | A | 0 |
| B. subtilis | A | 21d |
| S. pyogenes | D | 21 |
| M. avium | D | 0 |

*A = Streptomycin Assay Agar (BBL)
B = Nutrient Agar (BBL)
C = Pen-Assay Seed Agar (BBL)
D = Brain Heart Infusion Agar (Difco)
E = Syntnetic Medium (Mineral Salts - BBL)
F = Plate Count Medium (Difco)
G = Gray's Medium (Am. Type Culture Medium #855, AM. Type Culture Catalog of Strains (I), 1982
H = Schaedler Agar (Difco)

We claim:
1. A compound of the formula

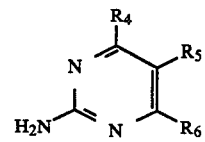

wherein
R$_4$ is chloro, bromo, aziridyl or 2-(1-aziridyl)ethylamino;
R$_5$ is hydrogen, fluoro, chloro, bromo, or iodo; and
R$_6$ is phenyl, with the proviso that when R$_4$ is chloro, R$_5$ is not hydrogen;
or where R$_4$ is chloro or bromo, a pharmacologically acceptable acid addition salt thereof.

2. A compound selected from the group consisting of:
4-(1-aziridyl)-6-phenyl-2-pyrimidinamine;
4-(1-aziridyl)-5-bromo-6-phenyl-2-pyrimidinamine;
N'-[2-(1-aziridyl)ethyl]-5-fluoro-6-phenyl-2,4-pyrimidinediamine;
4-chloro-5-fluoro-6-phenyl-2-pyrimidinamine or a pharmacologically acceptable acid addition salt thereof;
4,5-dichloro-6-phenyl-2-pyrimidinamine or a pharmacologically acceptable acid addition salt thereof;
4-chloro-5-iodo-6-phenyl-2-pyrimidinamine or a pharmacologically acceptable acid addition salt thereof;
4-chloro-5-bromo-6-phenyl-2-pyrimidinamine or a pharmacologically acceptable acid addition salt thereof.

3. The compound according to claim 2 consisting of 4-(1-aziridyl)-6-phenyl-2-pyrimidinamine.

4. The compound according to claim 2 consisting of 4-(1-aziridyl)-5-bromo-6-phenyl-2-pyrimidinamine.

5. The compound according to claim 2 consisting of N'-[2-(1-aziridyl)ethyl]-5-fluoro-6-phenyl-2,4-pyrimidinediamine.

6. The compound according to claim 2 consisting of 4-chloro-5-fluoro-6-phenyl-2-pyrimidinamine or a pharmacologically acceptable acid addition salt thereof.

7. The compound according to claim 2 consisting of 4,5-dichloro-6-phenyl-2-pyrimidinamine or a pharmacologically acceptable acid addition salt thereof.

8. The compound according to claim 2 consisting of 4-chloro-5-iodo-6-phenyl-2-pyrimidinamine or a pharmacologically acceptable acid addition salt thereof.

9. The compound according to claim 2 consisting of 4-chloro-5-bromo-6-phenyl-2-pyrimidinamine or a pharmacologically acceptable acid addition salt thereof.

* * * * *